(12) United States Patent
Aboerjaib

(10) Patent No.: US 12,303,284 B2
(45) Date of Patent: May 20, 2025

(54) SYSTEM AND METHOD FOR DETECTING BRAIN ABNORMALITIES USING BACKSCATTERED RADIATION

(71) Applicant: Sarah Y. Y. Aboerjaib, Kuwait (KW)

(72) Inventor: Sarah Y. Y. Aboerjaib, Kuwait (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 0 days.

(21) Appl. No.: 18/771,134

(22) Filed: Jul. 12, 2024

(65) Prior Publication Data

US 2025/0064376 A1 Feb. 27, 2025

Related U.S. Application Data

(60) Provisional application No. 63/534,126, filed on Aug. 23, 2023.

(51) Int. Cl.
*A61B 5/00* (2006.01)
(52) U.S. Cl.
CPC .......... *A61B 5/4064* (2013.01); *A61B 5/0059* (2013.01); *A61B 5/0082* (2013.01); *A61B 5/6803* (2013.01); *A61B 5/7264* (2013.01)
(58) Field of Classification Search
CPC ... A61B 5/0059; A61B 5/6814; A61B 5/0042; A61B 5/0075; A61B 5/0082; A61B 5/4064
See application file for complete search history.

(56) References Cited

U.S. PATENT DOCUMENTS 5,987,346 A * 11/1999 Benaron .............. A61B 5/1459
600/475
10,441,211 B1 * 10/2019 Hajjiah ................ A61B 5/4504
(Continued)

FOREIGN PATENT DOCUMENTS

WO WO-2024118999 A1 * 6/2024

OTHER PUBLICATIONS

John P Van Houten, et al., "Imaging Brain Injury Using Time-Resolved Near Infrared Scanning", Pediatric Research 39, 470-476 (1996), First available online Mar. 1, 1996.
(Continued)

*Primary Examiner* — Angela M Hoffa
*Assistant Examiner* — Younhee Choi
(74) *Attorney, Agent, or Firm* — Nath, Goldberg & Meyer; Joshua B. Goldberg

(57) ABSTRACT

At least one pulsed incident beam of light is directed toward a portion of the brain of a patient. At least one backscattered beam of light from the portion of the patient's brain is received and an insertion loss, $I_L$, is calculated as $$I_L = 20\log\frac{A_{BS}}{A_I},$$

where $A_{BS}$ is an amplitude of the at least one backscattered beam of light, and where $A_I$ is an amplitude of the at least one pulsed incident beam of light. An insertion phase difference, $I_{PD}$, is calculated as $I_{PD}=\phi_{BS}-\phi_I$, where $\phi_{BS}$ is a phase of the at least one backscattered beam of light, and where $\phi_I$ is a phase of the at least one pulsed incident beam of light. It is then determined if the patient has a brain abnormality based on the calculated insertion loss and the insertion phase difference.

16 Claims, 15 Drawing Sheets

(56) References Cited

U.S. PATENT DOCUMENTS

2014/0243681 A1* 8/2014 Hielscher ............ A61B 5/0075
                                                                             600/476
2021/0263320 A1* 8/2021 Seidman ................ G01S 17/04

OTHER PUBLICATIONS

Maurizio Ce, et al., "Artificial Intelligence in Brain Tumor Imaging: a Step toward Personalized Medicine", Curr Oncol. pp. 2673-2701, First available online Feb. 22, 2023.

Mahsa Arabahmadi, et al., "Deep Learning for Smart Healthcare—A Survey on Brain Tumor Detection from Medical Imaging", Sensors 2022, vol. 22, Issue 5, pp. 1-27, First available online Mar. 2, 2022.

Chaiyaporn Yuksen, et al. "Diagnostic properties of a portable near-infrared spectroscopy to detect intracranial hematoma in traumatic brain injury patients", European Journal of Radiology Open, vol. 7 (2020) 100246, pp. 1-4, First available online Jul. 29, 2020.

* cited by examiner

SYSTEM AND METHOD FOR DETECTING BRAIN ABNORMALITIES USING BACKSCATTERED RADIATION

CROSS-REFERENCE TO RELATED APPLICATIONS

This application claims the benefit of U.S. Provisional Patent Application No. 63/534,126, filed on Aug. 23, 2023, which is hereby incorporated by reference in its entirety.

BACKGROUND

Field

The disclosure of the present application relates to medical diagnostic tools, and particularly to a system and a method for detecting brain abnormalities using backscattered near infrared (NIR) light.

Description of Related Art

Computed tomography (CT) scan evaluations of detecting brain abnormalities are frequently conducted in hospitals and clinics for the purpose of determining if a brain has a hemorrhage (bleeding internally due to an injury), a stroke, a tumor, damage, or the like. The vast majority of these evaluations reveal normal brain tissue, and the injury in such cases is typically labeled as a soft-tissue trivial injury. In such cases, the CT scan evaluation was unnecessary, resulting in an unnecessary exposure to X-ray radiation, as well as an unnecessary hospital visit with associated costs. Moreover, the process of a CT scan is time-consuming and the delay in obtaining CT scan results could be fatal, potentially resulting in a patient's deterioration or death from a stroke before appropriate intervention can be applied.

While portable and relatively inexpensive non-X-ray diagnostic devices such as ultrasound devices exist, such devices typically either require expert training in interpreting signals/images or are intended for highly specialized purposes. Although ultrasound devices may be useful for their intended application of providing information about soft tissue structure and function, the characteristics of ultrasound make it unsuitable for high-quality diagnostic images of the brain. Thus, medical technology currently uses significantly more expensive, cumbersome, and potentially dangerous test methods such as a CT scan analysis to identify acute structural changes in the brain, such as those that appear in hemorrhages or tumors.

Although a number of devices that utilize ultrasound or electromagnetic energy to visualize or make determinations about certain properties of brain tissue exist, such devices typically do not provide for ease of use or accuracy. Brain tissues vary greatly in their distance from the skin to the underlying brain, and in the characteristics of the tissues between them. A need therefore exists for a simple, low-cost, and portable system which is tolerant of a large degree of variability in user technique, and which is capable of producing a sensitive and specific indication of the likelihood of a bleeding vessel in the area of a brain injury or an abnormal growth of cells within the brain.

Although backscatter radiation detectors are used for medical imaging, such detectors typically use X-rays, thus not only making them very expensive but potentially damaging to the tissue. Backscatter technology is based on the Compton scattering effect of X-rays. Unlike a traditional X-ray machine, which relies on the transmission of X-rays through the object, backscatter X-ray detects the radiation that reflects from the object and forms an image. The backscatter pattern is dependent on the material property and is good for imaging organic material. The organic material, however, is still exposed to the ionizing X-rays, thus making them potentially dangerous for use as a detector for sensitive tissue, such as brain tissue. Thus, a system and a method using the same for solving the aforementioned problems are desired.

SUMMARY

The system and method of detecting brain abnormalities in a brain of a patient using backscattered light use optical properties of the backscattered light to make determinations if the patient is suffering from a particular malady. At least one pulsed incident beam of light is generated using at least one light source. The at least one pulsed incident beam of light is directed toward a portion of the brain of the patient. At least one backscattered beam of light from the portion of the patient's brain is received and an insertion loss, $I_L$, is calculated as $$I_L = 20\log\frac{A_{BS}}{A_I},$$

where $A_{BS}$ is an amplitude of the at least one backscattered beam of light, and where Ar is an amplitude of the at least one pulsed incident beam of light. An insertion phase difference, $I_{PD}$, is calculated as $I_{PD}=\phi_{BS}-\phi_I$, where $\phi_{BS}$ is a phase of the at least one backscattered beam of light, and where $\phi$, is a phase of the at least one pulsed incident beam of light.

It is then determined if the patient has a brain abnormality based on the calculated insertion loss and the insertion phase difference. The brain of the patient is determined to have a hemorrhage when the calculated insertion loss is above a first loss threshold and the calculated insertion phase difference is lower than a first phase threshold; the brain of the patient is determined to have healthy brain tissue when the calculated insertion loss is lower than a second loss threshold and the calculated insertion phase difference is higher than a second phase threshold, the brain of the patient is determined to have at least one tumor if the calculated insertion loss is between the first and second loss thresholds and the calculated insertion phase difference is higher than the first and second phase thresholds; and the brain of the patient is determined to have an ischemic stroke if the calculated insertion loss is between the first and second loss thresholds and the calculated insertion phase difference is higher than the first and second phase thresholds but lower than that determined for the brain tumor.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
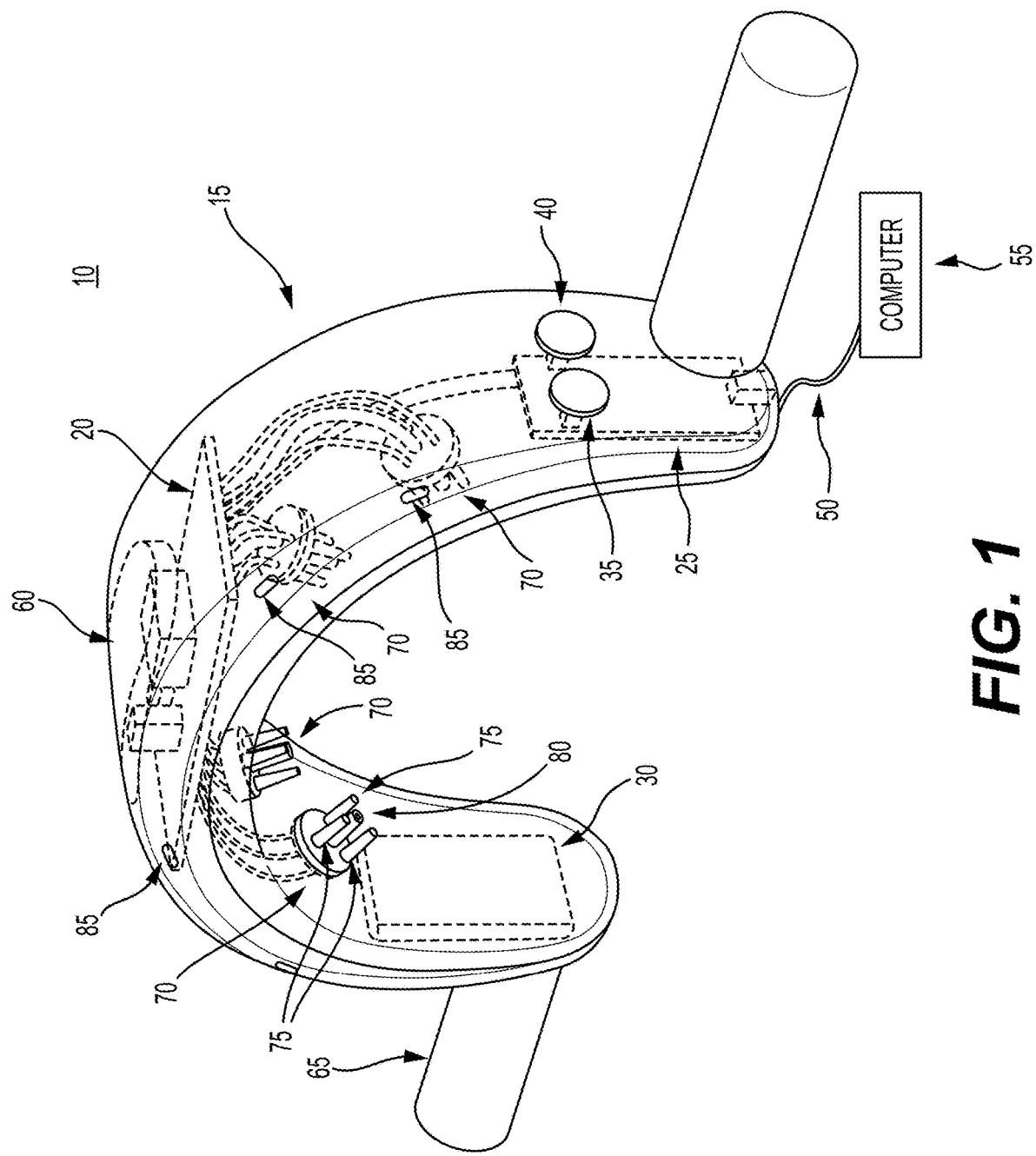
FIG. 1 is a perspective view of a system for detecting brain abnormalities.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment or diagnosis of a condition, disorder, or disease, such as diagnosis of a brain condition.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

FIGS. 1-4 depicts a system and a method for detecting brain abnormalities using backscattered near infrared (NIR) light for determining and detecting for the presence of any or all of a healthy brain, brain damage, brain tumor, brain hemorrhage, brain ischemic stroke, and the like. In this regard, FIGS. 1-4 show a system 10 for implementing the method of detecting brain abnormalities using backscattered NIR light includes a scalp-engaging optical interface structure in the form of a substantially U-shaped headband 15. Within a housing of the headband 15, there is a first printed circuit board assembly (PCBA) 20, a second printed circuit board assembly (PCBA) 25, a removable battery 30, and wiring connections. The second printed circuit board assembly 25, which is in communication with the first printed circuit board assembly 20 via the wiring connections, can include a calibration button 35 and a reset 40 configured for scanning of a healthy portion of a patient's brain 45 and diagnostic scanning for detecting brain abnormalities, respectively, as described herein.

In a non-limiting embodiment, the first printed circuit board assembly 20 can include a USB cable 50 attached thereto for connecting the headband 15 to a computer (i.e., personal computer, smartphone, smart tablet, other computers) 55 for data processing and analysis, thereby allowing the user to access the user interface for providing simple guided scan processes and display the results as described herein. While the USB cable 50 is used for connecting the headband 15 to the computer 55, it should be understood that other connection means such as Bluetooth® and Wi-Fi® can be substituted for the USB cable 50 without departing from the present subject matter.

In another non-limiting embodiment, the system 10 can include a wireless communication (i.e., Bluetooth®, Wi-Fi®, other wireless communications) for remote data transmission to cloud-based platforms thereby facilitating collaborative medical review and supporting telemedicine applications.

Situated above the first printed circuit board assembly 20 is an aluminum plate 60 configured for preventing temperature fluctuations on the first printed circuit board assembly 20. In certain embodiments, the aluminum plate 60 can be embedded fully within the housing of the headband 15. In other embodiments, the aluminum plate 60 can be partially exposed on the exterior surface of the housing of the headband 15. In a further non-limiting embodiment, the headband 15 can have a dimension of about 70 mm in width (W), about 140 mm in height (H), and about 380 mm in length (L).

On the outer exterior surfaces of the housing of the headband 15, there are at least two handles 65 attached to the sides of the headband 15 for allowing a user to place the headband 15 on the patient's head, thereby permitting measurements of the patient's brain 45 as described herein. A display screen with a user interface integrated therein is located on the outer exterior surface of the housing of the headband 15. The user interface is configured to guide the user through the calibration process as described herein, direct the user to the scanning process across different regions of interest on the patient's brain, and display the type of brain abnormalities detected.

On the inner exterior surfaces of the housing of the headband 15, there are a plurality of elements 70 mounted thereon which are individually in communication with each of a plurality of light sources on the first printed circuit board assembly 20, as described herein. Each of the plurality of elements 70 can include a plurality of light projections 75 and a receiver 80 mounted thereon configured for directing incident beams of near infrared light (IBNIR) from the respective plurality of light sources onto a portion of the patient's brain 45 and receiving backscattered beams of near infrared light (BSBNIR) from the portion of the patient's brain 45, respectively, as described herein. In a non-limiting embodiment, the plurality of light projections 75 can be laser projections.

On the front exterior surfaces of the housing of the headband 15, there is a plurality of LED light indicators 85 corresponding to each of the plurality of elements 70 configured to indicate the type of brain abnormalities detected (i.e., brain damage, brain tumor, brain hemorrhage, ischemic stroke) or the detection of a healthy brain as described herein. In certain non-limiting embodiments, the plurality of LED light indicators 85 can include a green LED configured to indicate a healthy brain, a red LED configured to indicate a brain hemorrhage, an orange LED configured to indicate a brain tumor, a yellow LED configured to indicate a brain ischemic stroke, a purple LED configured to indicate a brain damage, and a blue LED configured to indicate calibration mode. It should be understood that while each of the mentioned colors have been assigned for the respective brain conditions and calibration mode in one embodiment, other colors may be assigned to the respective brains conditions and calibration mode without departing from the present subject matter.

Figure 4:
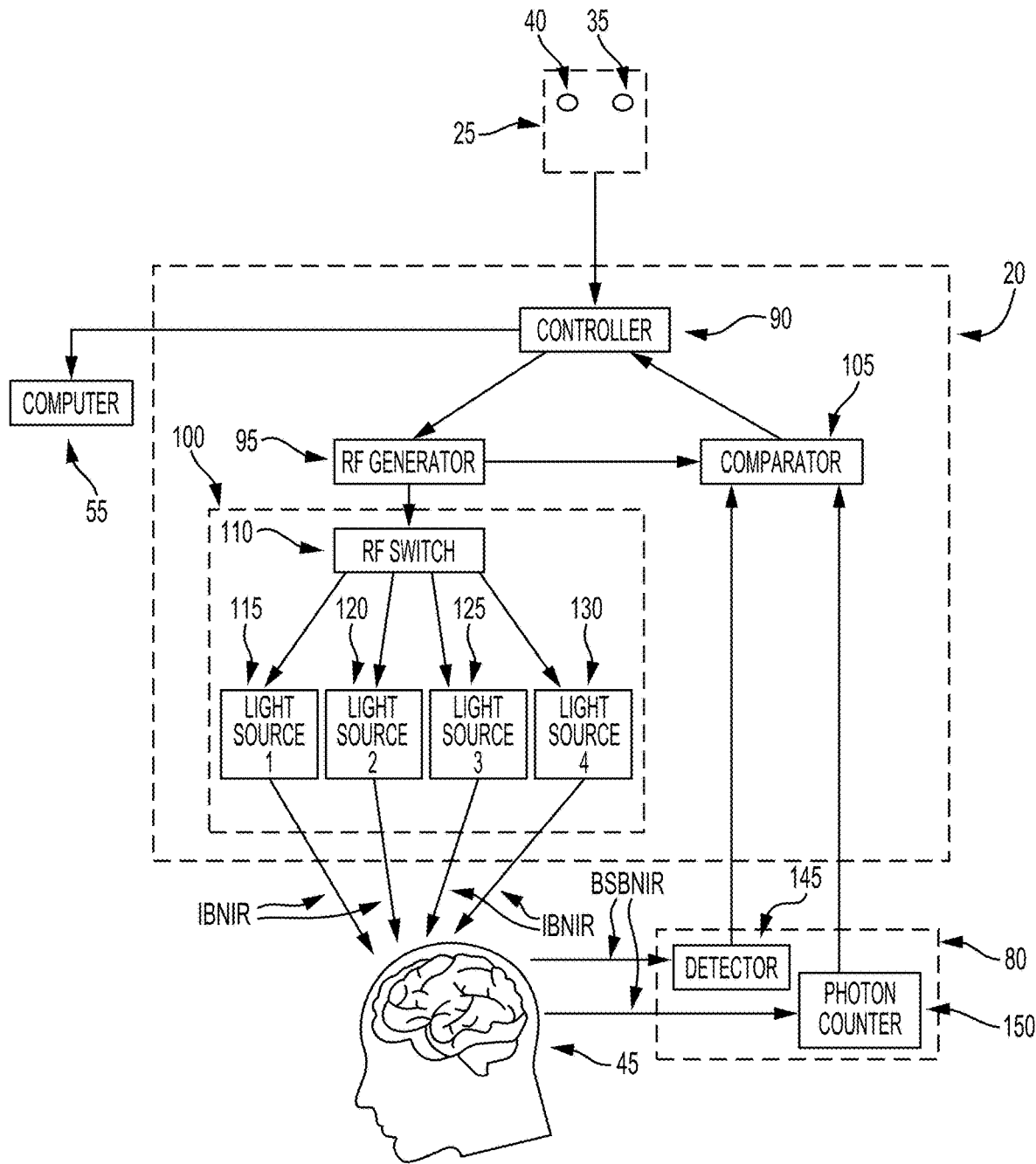
FIG. 4 is a block diagram of various subcomponents of the system of FIG. 1 and a method for detecting brain abnormalities using backscattered light.

As shown in FIG. 4, the mentioned first printed circuit board assembly 20 can include a controller 90, a radio frequency (RF) generator 95, a transmitter 100, and a comparator microchip 105. The controller 90 is configured to send a signal to the RF generator 95 to generate pulsing incident beams of functional near-infrared light (IBNIR) coming from the transmitter 100 onto the patient's brain 45. While FIG. 4 shows the patient's brain 45, it should be understood that the patient's brain 45 is shown for exemplary purposes only. The transmitter 100, which in certain non-limiting embodiments can be a vertical-cavity surface-emitting laser (VCSEL) or a Fabry-Perot laser, can include a radio frequency (RF) switch 110 and at least one light source for generating a pulsing incident beam of functional near infrared light (IBNIR). The RF switch 110 can be a SP3T RF switch manufactured by the Hittite Microwave Corporation of Massachusetts, as a non-limiting example. The at least one light source can be a multi-wavelength laser or light emitting diode (LED) source.

In a particular non-limiting example, the at least one light source can be a vertical-cavity surface-emitting laser (VCSEL), as a non-limiting example, which can include a first light source 115, a second light source 120, a third light source 125, and a fourth light source 130, which can respectively generate functional near infrared light (fNIR) at wavelengths of about 650 nm to about 680 nm, about 760 nm, about 850 nm, and about 980 nm. In certain embodiments, this first wavelength can be any of 650 nm, 670 nm, and 680 nm. These wavelengths of fNIR have been used for spectroscopic measurements of brain tissue and can be used to accurately detect levels of oxygenated and deoxygenated hemoglobin using the properties of light absorption and scattering.

The RF generator 95, which has a broadband frequency of about 30 MHz to about 1000 MHz, can be in communication with the RF switch 110 to modulate the first light source 115, the second light source 120, the third light source 125, and the fourth light source 130 thereby generating pulsing incident beams of functional near infrared light (IBNIR) at the respective wavelengths mentioned with the mentioned broadband frequency range. The RF generator 95 can be an Anritsu MS4623B network analyzer manufactured by the Anritsu Corporation of Japan, as a non-limiting example. The pulsing of the incident beam(s) can lead to deeper penetration than a non-pulsed beam and can further allow for targeted absorption of the beam(s), as well as providing the ability to gather specific information about the brain structure(s). RF pulsing, as a non-limiting example, can enhance the efficiency of the transmission of the light signals through the tissues, resulting in improved penetration depth and enhancing the interaction between photons and tissue components, leading to better imaging capabilities.

Figure 5:
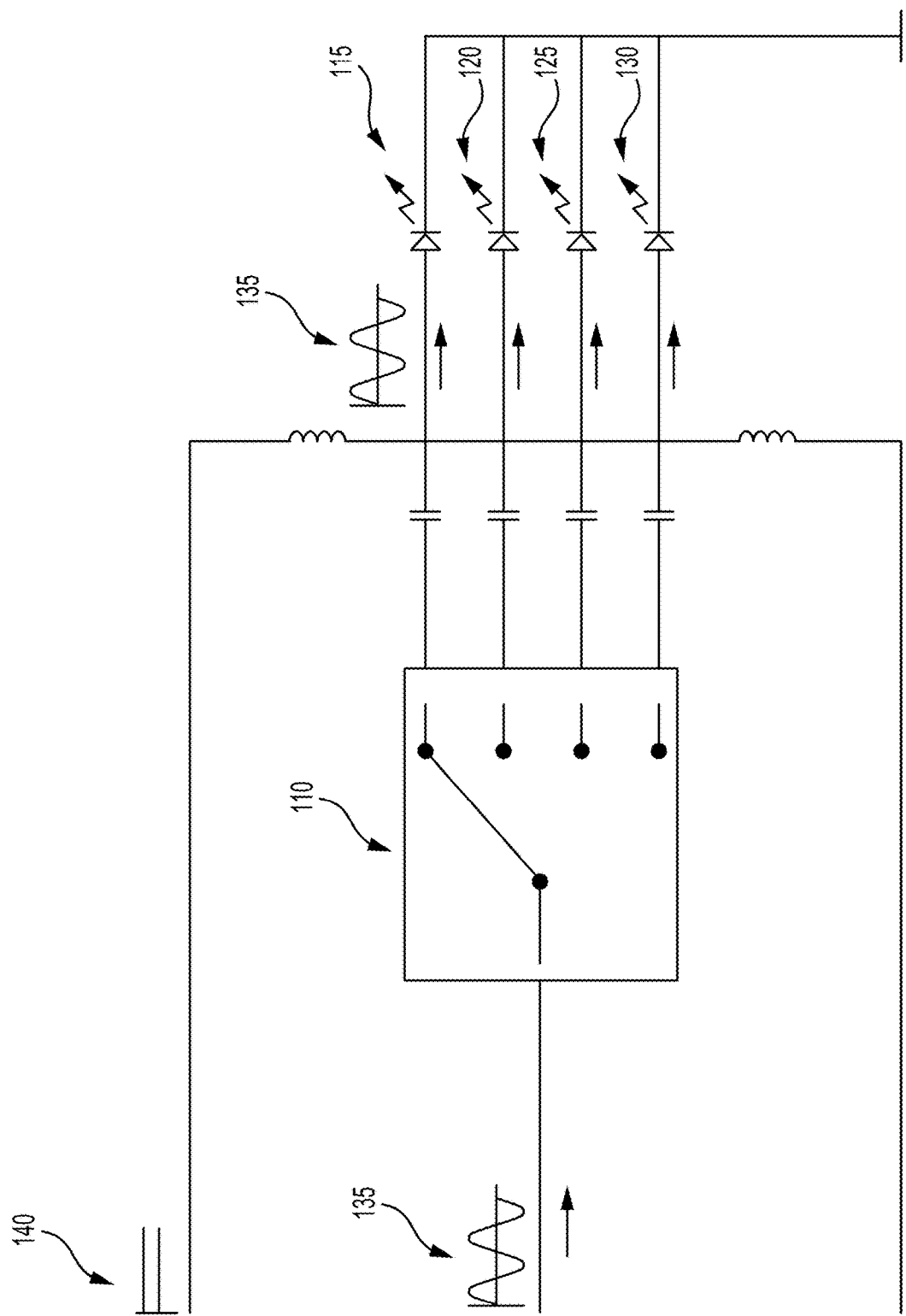
FIG. 5 is a circuit diagram of a radio frequency (RF) switch and a plurality of light sources of the system of FIG. 4.

As shown in FIG. 5, the RF generator 95 can produce a fixed RF frequency using an onboard voltage-controlled oscillator (VCO) which can be trimmed to any frequency in a range of about 150 MHz to about 200 MHz using a potentiometer. The output of the VCO is fed into a dual stage amplifier to amplify the signal four times resulting in an RF signal amplitude 135 going to the RF switch 110. In some non-limiting embodiments, the RF signal amplitude 135 is about 1.6 Vpp (+8 dBm). The RF switch 110 can sequentially relay the RF signal amplitude 135 to each of the first light source 115, the second light source 120, the third light source 125, and the fourth light source 130 individually via a bias T network. The first light source 115, the second light source 120, the third light source 125, and the fourth light source 130 are also supplied with a DC bias current 140 concurrently with receiving the RF signal amplitude 135 for modulating all of the mentioned light sources. In a non-limiting embodiment, the DC bias current 140 is about 30 mA.

Referring back to FIG. 4, the pulsing incident beams of functional near infrared light (IBNIR), which are generated by the transmitter 100 and are directed toward a portion of the patient's brain 45, have both an incident amplitude, $A_I$, and an incident phase, $\phi_I$, associated therewith. Resultant backscattered beams of near infrared light (BSBNIR) are received by the receiver 80, which converts the received backscattered beams of near infrared light (BSBNIR) into a signal representative of a backscattered amplitude, $A_{BS}$, and a backscattered phase, $\phi_{BS}$. In another non-limiting embodiment, the distance between the transmitter 100 and the receiver 80 can be set at about 1 cm, although it should be understood that the penetration depth may be increased by decreasing this distance. The transmitter 100 can be a pulsing multi-wavelength VCSEL, module No. V3WLM-002 manufactured by Vixar Inc. of Minnesota, as a non-limiting example. The receiver 80 can include a detector 145 and a photon counter 150. The detector 145 can be an avalanche photodiode (APD) detector, model No. C5658 manufactured by Hamamatsu® Photonics K.K. Corporation of Japan. The photon counter 150 can be model No. H8259-02 also manufactured by Hamamatsu® Photonics K.K. Corporation of Japan, as a non-limiting example.

Figure 6:
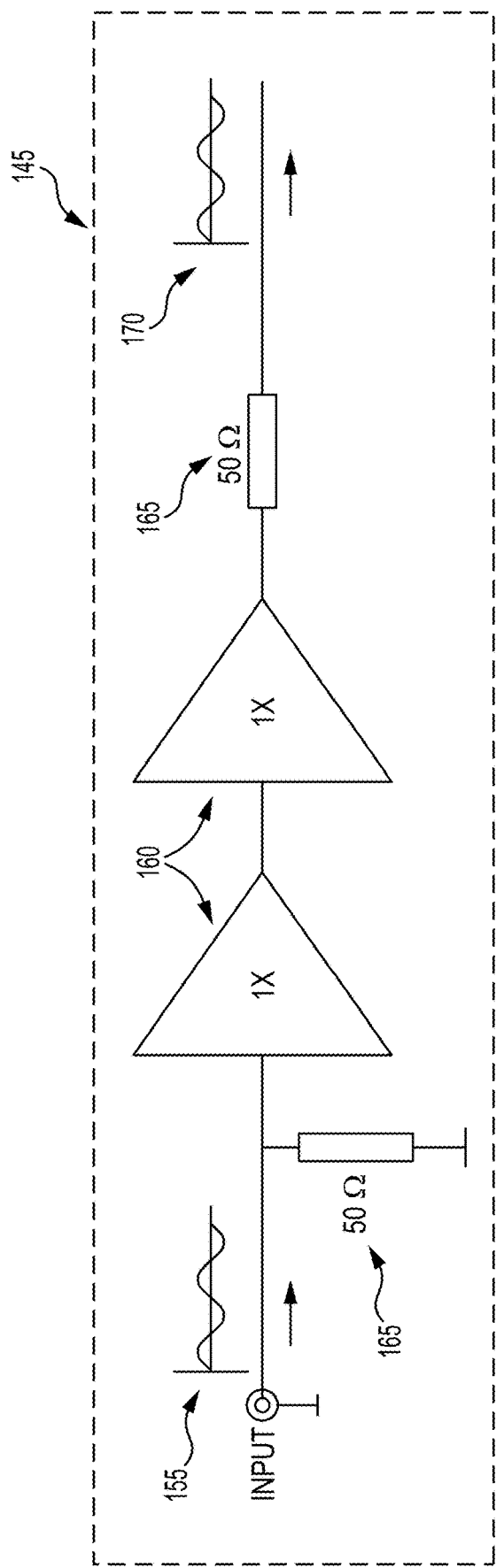
FIG. 6 is a circuit diagram of a detector of the system of FIG. 4.

As shown in FIG. 6, signals 155 of the backscattered beams of near infrared light (BSBNIR) are received by the detector 145 to be amplified by amplifiers 160 and then buffered with a 5002 input buffer 165 to maintain signal integrity, thereby generating buffered signals 170 of the backscattered beams of near infrared light (BSBNIR).

Figure 7:
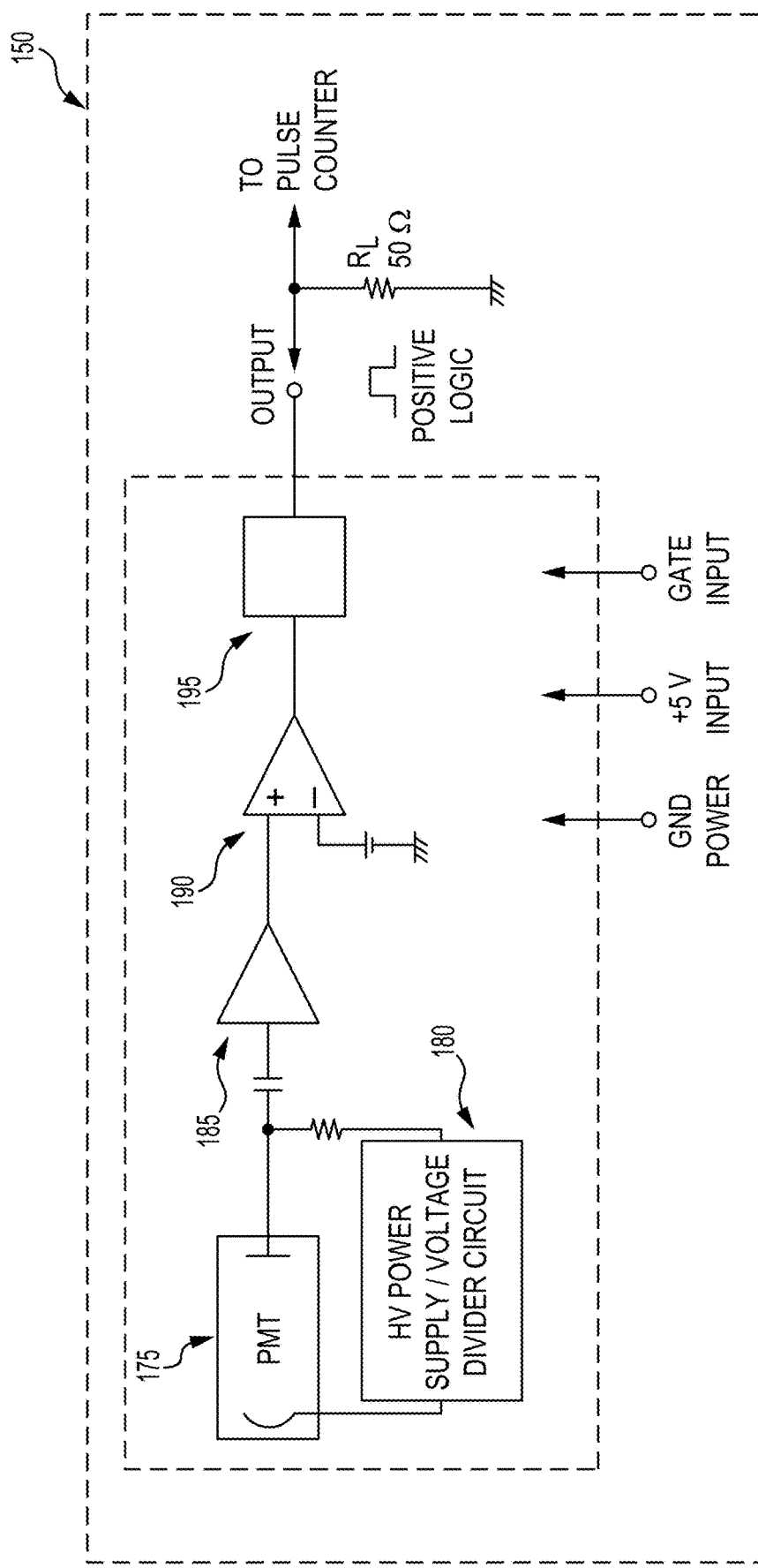
FIG. 7 is a circuit diagram of a photon counter of the system of FIG. 4.

FIG. 7 shows a block diagram of the photon counter 150 model No. H8259-02. The photon counter 150 is configured to measure the number of photons detected from the backscattered beams of near infrared light (BSBNIR). The photon counter 150 can include a photomultiplier tube (PMT) (175), a high voltage power supply/voltage divider circuit 180, an amplifier 185, a comparator 190, and a pulse shaper 195. To improve reliability of the measurements, a timing module within the photon counter 150 is synchronized with the first light source 115, the second light source 120, the third light source 125, and the fourth light source 130. This synchronization allows for time correlated photon counting by distinguishing between scattered photons and potential background noises. In a further non-limiting embodiment, the timing module is a time of flight (ToF) sensor module.

The backscattered amplitude ($A_{BS}$) and the backscattered phase ($\phi_{BS}$) of the backscattered beams of near infrared light (BSBNIR) can be measured by the comparator microchip 105, allowing an insertion loss ($I_L$), an insertion phase difference ($I_{PD}$), and time-delay to be calculated by the controller 90 as shown in FIG. 4. The controller 90 may be any suitable controller, such as a processor or a programmable logic controller. The insertion loss ($I_L$), which is absorption of the near-infrared light as it interacts with the brain tissues, can be calculated as $$I_L = 20\log\frac{A_{BS}}{A_I}.$$

The insertion phase difference ($I_{PD}$), which is scattering of the near-infrared light as it interacts with the brain tissues, can be calculated as $I_{PD}=\phi_{BS}-\phi_I$.

Figure 8:
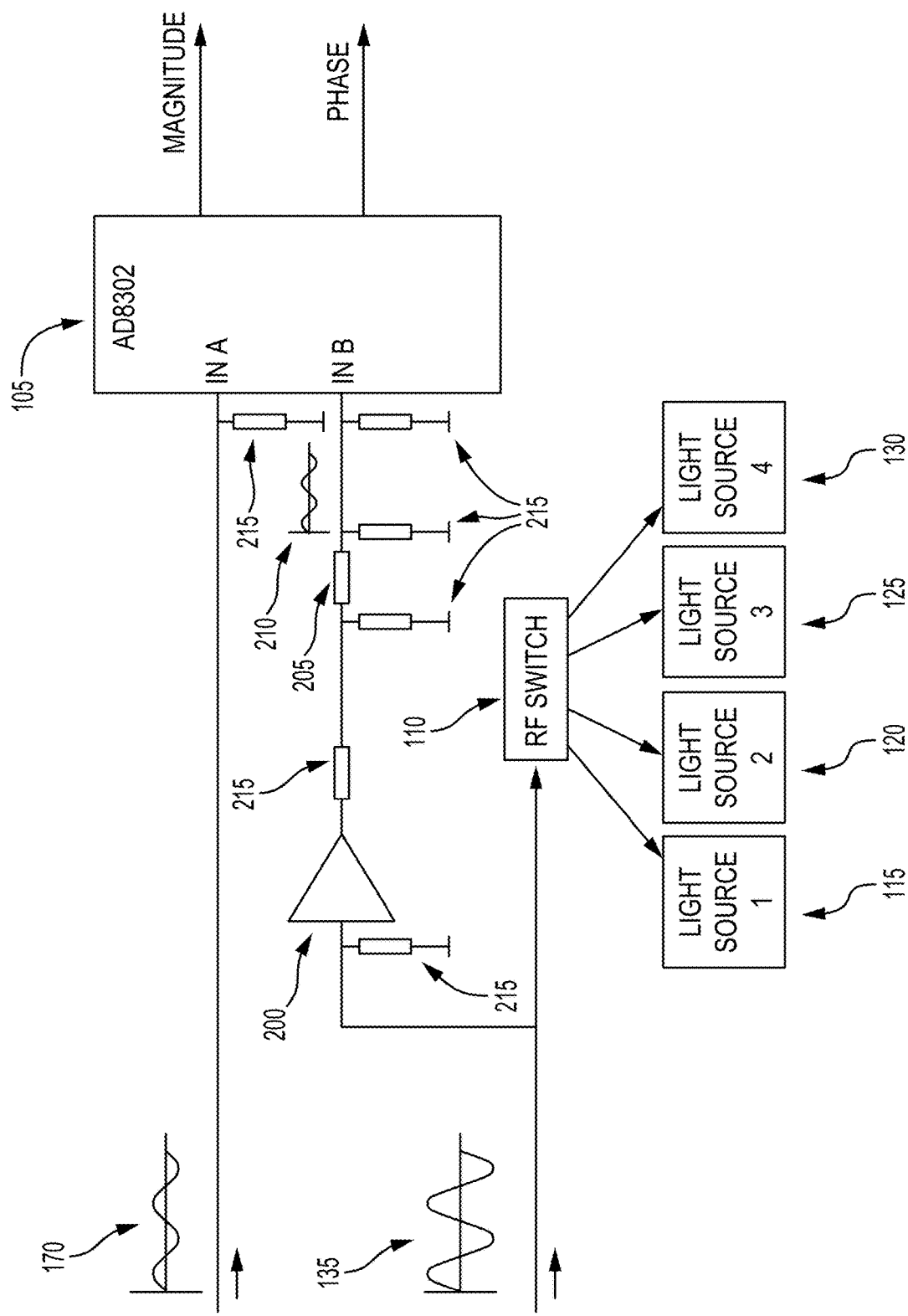
FIG. 8 is a circuit diagram showing how the signals from the detector and an RF generator are being processed by a comparator chip of the system of FIG. 4.

As shown in FIG. 8, the buffered signals 170 of the backscattered beams of near infrared light (BSBNIR) from the detector 145 are compared with the RF signal amplitude 135 from the RF generator 95 by sending the respective signals to the comparator chip 105, which may be a magnitude and phase detector integrated circuit model No. AD8302 from Analog Devices, as a non-limiting example, for analyzing the difference in magnitude and phase. Specifically, a portion of the RF signal amplitude 135 is sent to the RF switch 110 for modulating the first light source 115, the second light source 120, the third light source 125, and the fourth light source 130 as mentioned above. Another portion of the RF signal amplitude 135 is sent to a buffer 200 and then to an attenuator 205 to generate an attenuated buffered RF signal amplitude 210 prior to being processed by the comparator chip 105. The comparator chip 105 can include a plurality of 5002 resistors 215. As a result of processing the buffered signals 170 of the backscattered beams of near infrared light (BSBNIR) and the attenuated buffered RF signal amplitude 210, the comparator chip 105 generates two output analog voltages called magnitude (Tx) and phase (Rx) expressed in decibels (dB). The two output analog voltages are connected with an A/D converter of an Arduino controller, as a non-limiting example, for further processing.

As mentioned above, the controller 90 is configured to calculate the insertion loss ($I_L$) and insertion phase difference ($I_{PD}$) as shown in FIG. 4. The determination of whether or not the patient has a healthy brain or brain abnormalities (i.e., brain tumor, brain hemorrhage, ischemic stroke, etc.)

can be based on the calculated insertion loss ($I_L$), the calculated insertion phase difference ($I_{PD}$), or both.

In certain embodiments, it can be determined that the patient's brain 45 has a hemorrhage, which is a condition of elevated pooled blood and oxygenated hemoglobin due to damaged blood vessels and therefore absorbs higher NIR light, if the calculated insertion loss ($I_L$) is above a first loss threshold (first loss threshold is based on NIR imaging results from patient populations in clinical trials, represents typical absorption level of NIR light for brain hemorrhage condition) and/or the calculated insertion phase difference ($I_{PD}$) is lower (due to homogenous low scattering level of NIR light caused by the pool blood) than a first phase threshold (first phase threshold is based on NIR imaging results from patient populations in clinical trials, represents typical scattering level of NIR light for brain hemorrhage condition).

In other embodiments, it can be determined that the patient's brain 45 has healthy brain tissues, which have less dense structure compared to brain tissues affected by hemorrhages and therefore absorb minimal NIR light, if the calculated insertion loss ($I_L$) is lower than a second loss threshold (second loss threshold is based on NIR imaging results from patient populations in clinical trials, represents typical absorption level of NIR light for normal brain tissues) and/or the calculated insertion phase difference ($I_{PD}$) is higher (due to the complex structure of the healthy cerebral cortex of the brain which leads to uniform scattering level of the NIR light) than a second phase threshold (second phase threshold is based on NIR imaging results from patient populations in clinical trials, represents typical scattering level of NIR light for normal brain tissues).

In additional embodiments, it can be determined that the patient's brain 45 has a tumor, which is a condition with irregular and heterogeneous composition within the brain tissues and therefore absorbs NIR light less than brain hemorrhage and more than heathy brain tissues, if the calculated insertion loss ($I_L$) is between the first and second loss thresholds and/or the calculated insertion phase difference ($I_{PD}$) is higher than the first and second phase thresholds.

In still other embodiments, it can be determined that the patient's brain 45 has an ischemic stroke, which is a condition that causes blood flow reduction and deoxygenated hemoglobin concentrations and therefore absorbs NIR light less than brain hemorrhage and more than heathy brain tissues, if the calculated insertion loss ($I_L$) is between the first and second loss thresholds and/or the calculated insertion phase difference ($I_{PD}$) is higher than the first and second phase thresholds but not as high as for the brain tumor.

Figure 2:
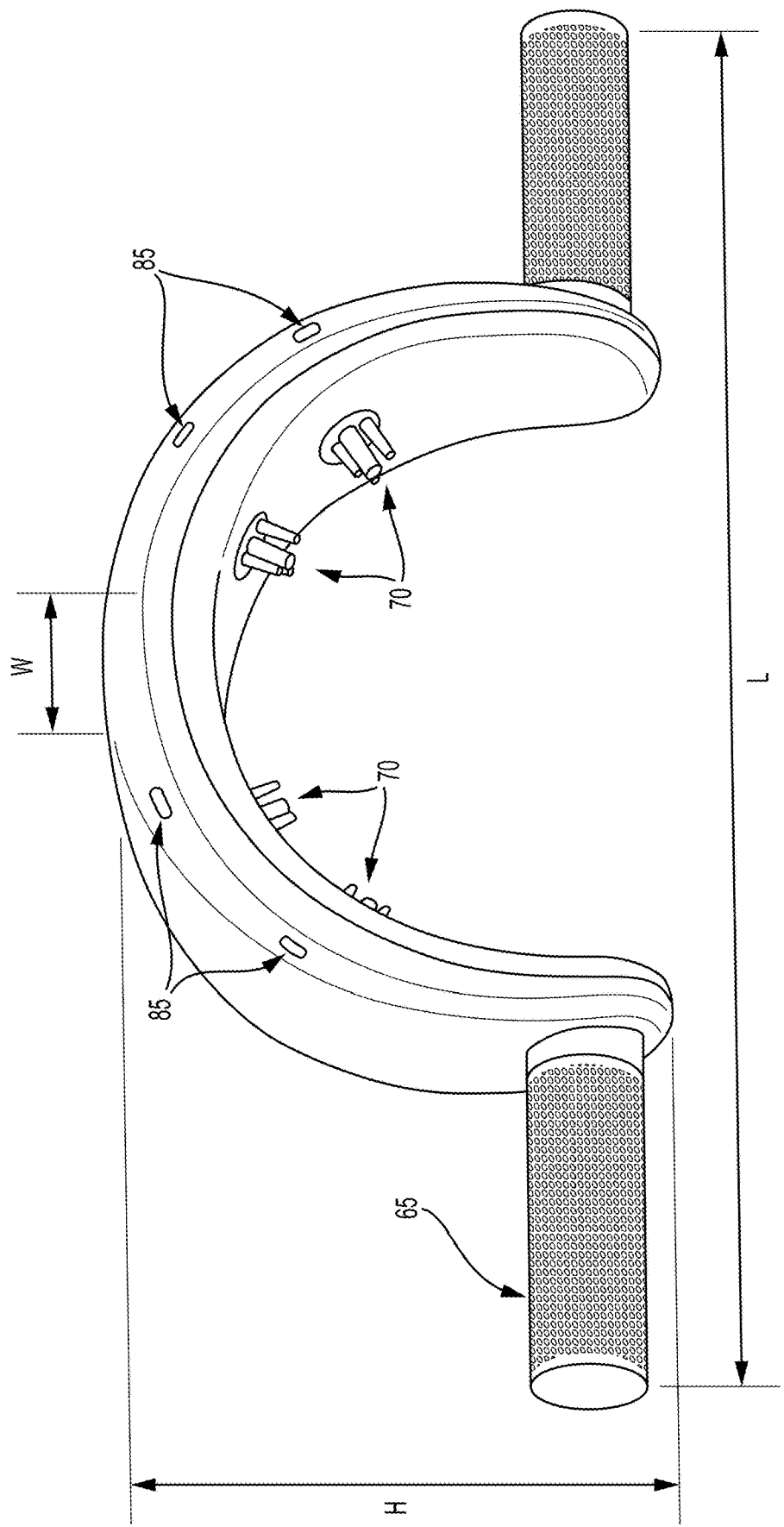
FIG. 2 is a front view in section of the system of FIG. 1.
Figure 3:
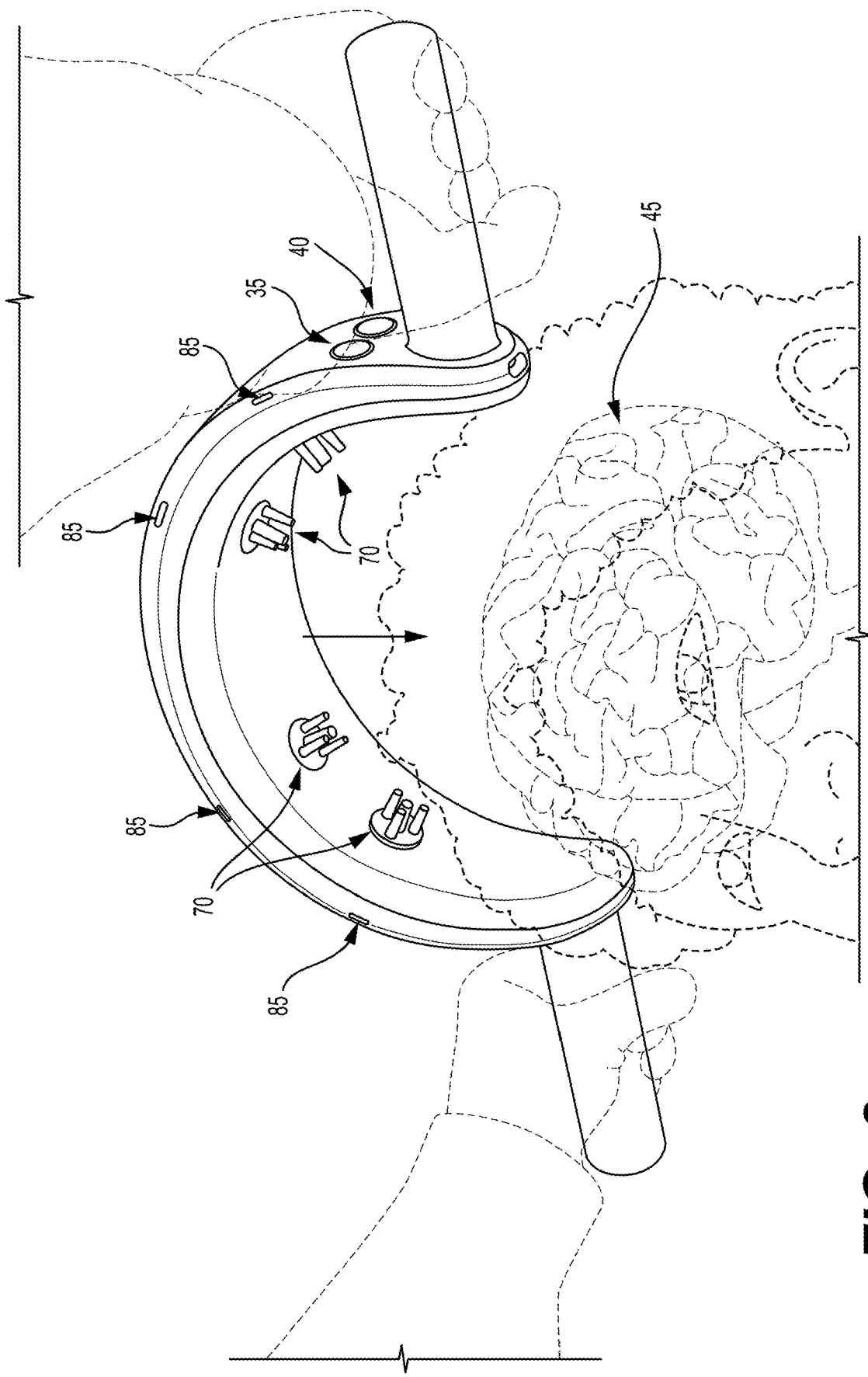
FIG. 3 is a front view in section of the system of FIG. 1, shown being placed on a patient's head.

As a non-limiting example, a machine learning system, which can be within the controller 90, can be trained with the first loss threshold, the second loss threshold, the first phrase threshold, and the second phrase threshold. This machine learning system can be used to compare the calculated insertion loss ($I_L$) and insertion phase difference ($I_{PD}$) against the training data. Based on determination of the type of brain abnormality (i.e., healthy brain, brain damage, brain tumor, brain hemorrhage, brain ischemic stroke, etc.) from the comparison, the controller 90 can activate the respective LED color (i.e., green, red, orange, yellow, or purple) from the plurality of LED light indicators 85 as shown in FIGS. 1-3. It should be understood that any suitable hardware and/or software may be used for performing the determination.

As non-limiting examples, supervised learning and/or unsupervised learning techniques may be used, either alone or in combination with deep learning algorithms, allowing for effective analysis of the signals obtained from the patient's brain. The use of machine learning allows for fine tuning and optimization to improve the accuracy, sensitivity, and specificity of the system, resulting in not only automated detection of brain abnormalities, but also reducing the risk of human error. It should also be understood that while the comparison can be completed with a machine learning system as described herein, other systems such as Monte Carlo simulations and fuzzy logic can be used without departing from the present subject matter.

In one embodiment, the method of detecting brain abnormalities using backscattered NIR light for determining a healthy brain, brain damage, brain tumor, brain hemorrhage, brain ischemic stroke, and the like starts with the user placing the headband 15 on the patient's head to permit interaction with the user's brain 45 as shown in FIG. 3. According to this embodiment, the placement of the headband 15 is initially on the healthy side of the patient's brain 45. The user then presses the calibration button 35 on the headband 15, which actives the blue LED from the plurality of LED light indicators 85, to initiate a scan of the healthy side of the patient's brain 45 to establish a baseline thereby calibrating the system 10 by capturing the optical properties of the brain tissues that are considered normal for the patient. In certain embodiments, the baseline can serve as a predefined threshold for comparing with subsequent insertion loss ($I_L$) and insertion phase difference ($I_{PD}$) readings thereby enabling determination of the type of brain abnormalities as described herein. Once the threshold is established according to this embodiment, the user can reposition the headband 15 to correspond to the symptomatic region of the patient's brain 45 where the brain abnormalities may occur. Then, the user can press the reset button 40 to initiate diagnostic scanning of the patient's brain for detecting brain abnormalities.

As shown in FIGS. 4-5, once the reset button 40 is pressed, the process for performing detecting brain abnormalities begins with the controller 90 sending a signal to the RF generator 95 to generate the RF signal amplitude 135 to be sent to the RF switch 110 for modulating the first light source 115 (Step 1). Concurrently, the controller 90 initiates the DC bias current 140 to be sent to the first light source 115 to generate a pulsing incident beam of functional near infrared light (IBNIR) at a wavelength of about 650 nm to about 680 nm (Step 2). The pulsing incident beam of functional near infrared light (IBNIR) from the first light source 115 is directed toward the symptomatic region of the patient's brain 45 (Step 2). Then, backscattered beam of near infrared light (BSBNIR) coming from the patient's brain 45 is detected by the detector 145 and the photon counter 150 as shown in FIGS. 4 and 6-7 (Step 3). Signal 155 of the backscattered beam of near infrared light (BSBNIR) can be amplified and buffered by the detector 145 to generate buffered signal 170 of the backscattered beam of near infrared light (BSBNIR) as shown in FIG. 6 (Step 4). Next, the buffered signal 170 of the backscattered beam of near infrared light (BSBNIR) from the detector 145 is compared with the RF signal amplitude 135 from the RF generator 95 by sending the respective signals to the comparator chip 105 to generate output analog voltage readings in terms of magnitude and phase as shown in FIGS. 4 and 8 (Step 5). Afterward, the magnitude and voltage readings are sent to the controller 90 to calculate the insertion loss ($I_L$) and the insertion phase difference ($I_{PD}$) (Step 6). Thereafter, the calculated insertion loss ($I_L$) and the insertion phase difference ($I_{PD}$) are stored in a data storage module within the controller 90 (Step 7). Subsequently, steps 1-7 are repeated for the second light source 120, the third light source 125, and the fourth light source 130 at the respective wavelengths of about 760 nm, about 850 nm, and about 950 nm.

Once all the insertion loss ($I_L$) and the insertion phase difference ($I_{PD}$) data are calculated for all the light sources, those data can be compared with the training data (i.e., the first loss threshold, the second loss threshold, the first phrase threshold, and the second phrase threshold) from the machine learning system. Based on the determination of the type of brain condition (i.e., healthy brain, brain damage, brain tumor, brain hemorrhage, brain ischemic stroke, and the like) from the comparison, the controller 90 can activate the respective LED color (i.e., green, red, orange, yellow, or purple) from the plurality of LED light indicators 85 as shown in FIGS. 1-3.

Figure 9:
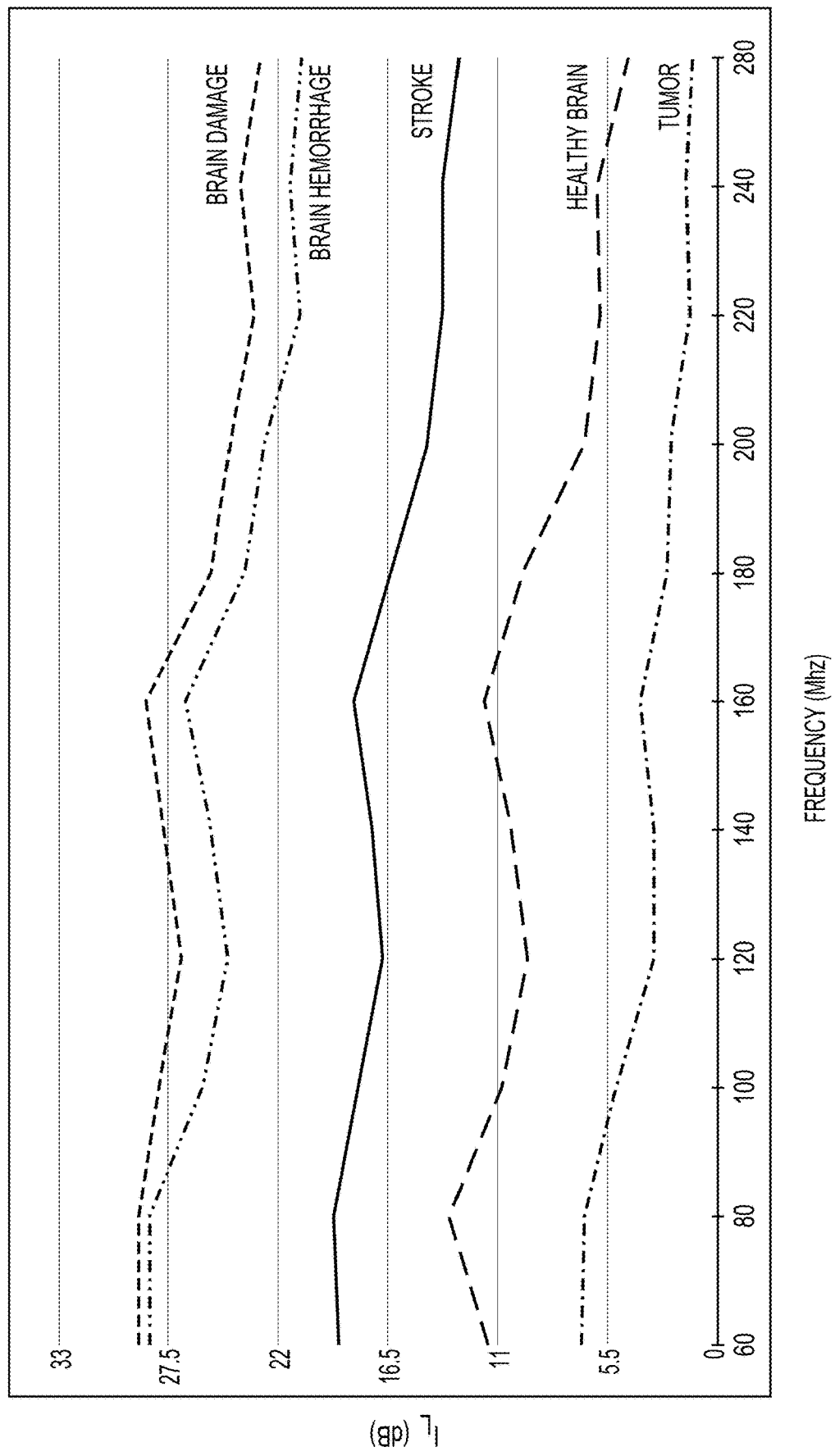
FIG. 9 is a graph comparing insertion loss results for the method of detecting brain abnormalities using backscattered light for cases including a healthy brain, brain damage, brain tumor, brain hemorrhage, and brain ischemic stroke.
Figure 10:
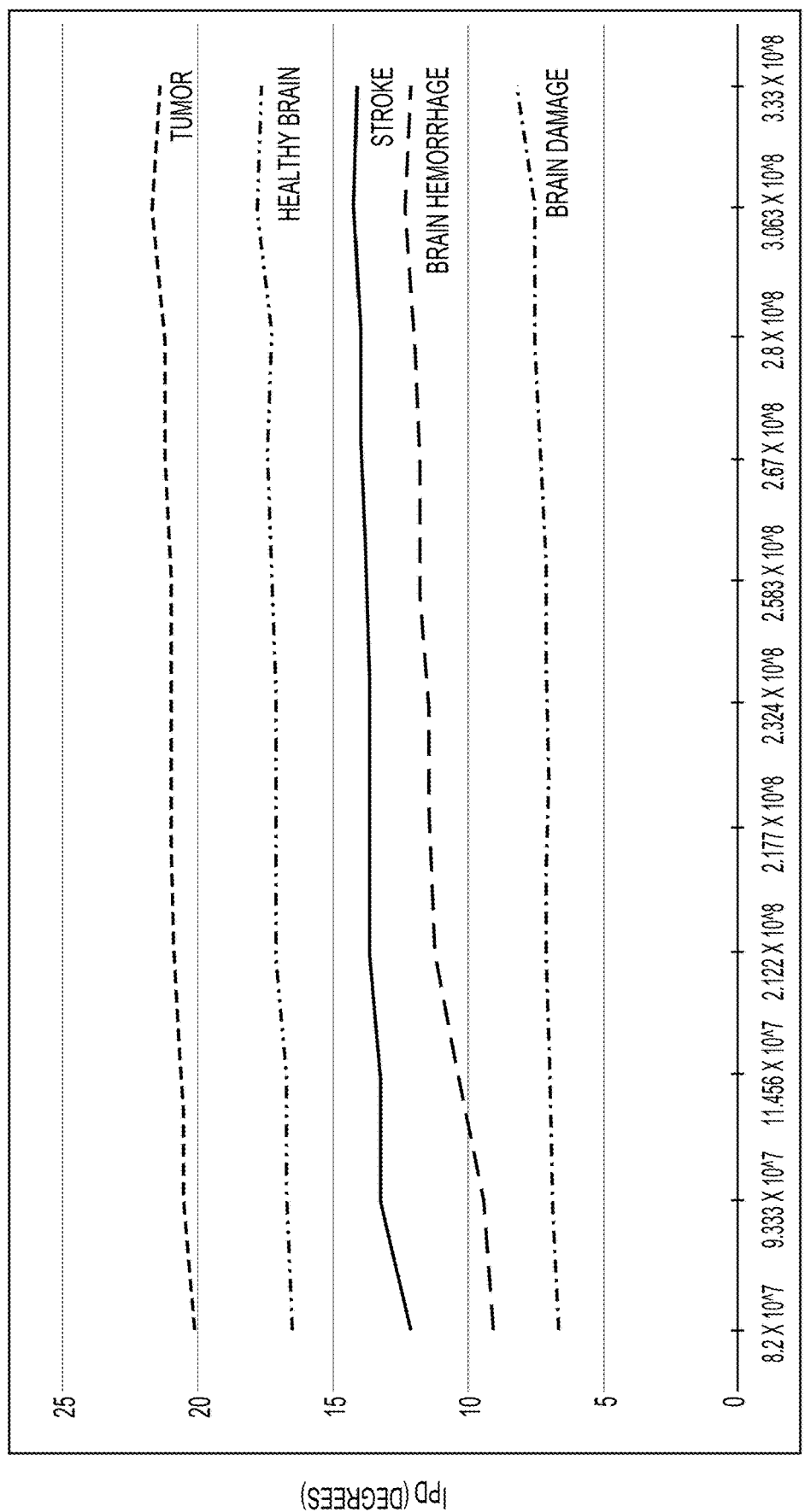
FIG. 10 is a graph comparing insertion phase difference results for the method of detecting brain abnormalities using backscattered light for cases including a healthy brain, brain damage, brain tumor, brain hemorrhage, and brain ischemic stroke.
Figure 11:
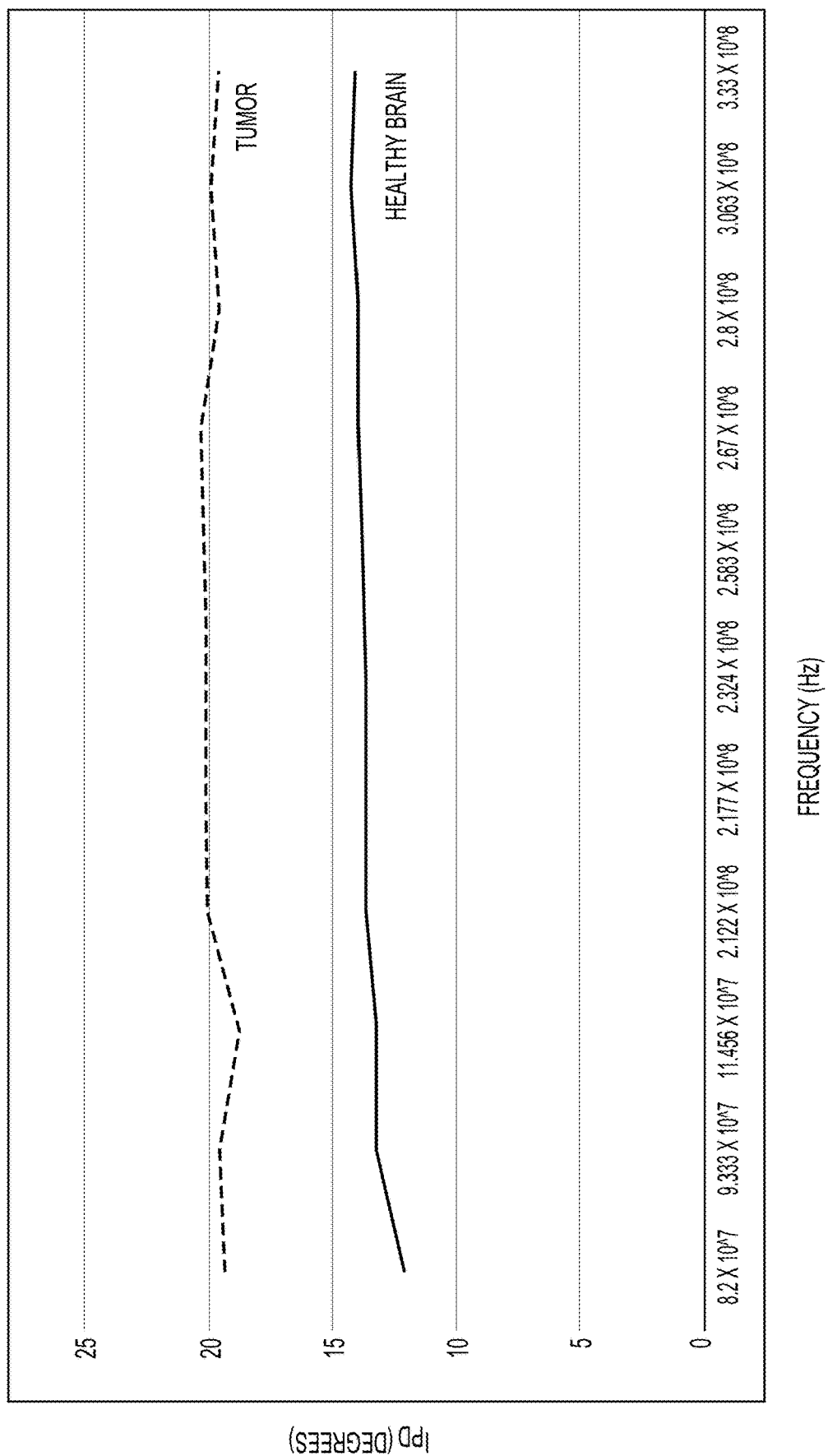
FIG. 11 is a graph comparing insertion phase difference results for the method of detecting brain abnormalities using backscattered light for cases including a healthy brain and a brain tumor.

FIGS. 9-11 depict the insertion loss ($I_L$) and the insertion phase difference ($I_{PD}$) for the detected brain abnormalities over a frequency range. As shown in FIG. 9, brain damage has the highest insertion loss ($I_L$) across the entire frequency range. On the other hand, brain tumors (measured with India ink) have the lowest insertion loss ($I_L$) across the entire frequency range. Shown in FIG. 10, brain tumors have the highest insertion phase difference ($I_{PD}$) across the entire frequency range. Conversely, brain damage (measured with India ink) has the lowest insertion phase difference ($I_{PD}$) across the entire frequency range. FIG. 11 shows that brain tumors have the highest insertion phase difference ($I_{PD}$) across the entire frequency range. Conversely, a healthy brain (measured with no India ink) has the lowest insertion phase difference ($I_{PD}$) across the entire frequency range. The India ink as described herein was used to simulate human blood. Corresponding data are shown in Tables 1-3, respectively showing the data for insertion loss ($I_L$) and insertion phase difference ($I_{PD}$).

TABLE 1

Insertion Loss Data (in dB)

| Frequency (MHz) | Healthy Brain | Tumor | Stroke | Brain Hemorrhage | Brain Damage |
|---|---|---|---|---|---|
| 60 | 11.44 | 6.78 | 18.98 | 28.44 | 28.95 |
| 80 | 13.43 | 6.70 | 19.23 | 28.43 | 28.98 |
| 100 | 10.81 | 5.07 | 17.90 | 25.81 | 27.99 |
| 120 | 9.51 | 3.23 | 16.78 | 24.51 | 26.85 |
| 140 | 10.34 | 3.20 | 17.30 | 25.34 | 27.72 |
| 160 | 11.63 | 3.90 | 18.22 | 26.63 | 28.63 |
| 180 | 9.73 | 2.52 | 16.38 | 23.73 | 25.33 |
| 200 | 6.68 | 2.33 | 14.48 | 22.68 | 24.44 |
| 220 | 5.90 | 1.39 | 13.79 | 20.90 | 23.23 |
| 240 | 6.00 | 1.55 | 13.72 | 21.42 | 23.90 |
| 280 | 4.50 | 1.32 | 12.99 | 20.80 | 22.89 |

TABLE 2

Insertion Phase Difference Phase (in degrees)

| Frequency (Hz) | Brain Damage | Brain Hemorrhage | Stroke | Healthy Brain | Tumor |
|---|---|---|---|---|---|
| $8.2 \times 10^7$ | 6.67 | 9.10 | 12.13 | 16.51 | 20.12 |
| $9.333 \times 10^7$ | 6.86 | 9.44 | 13.23 | 16.69 | 20.53 |
| $11.456 \times 10^7$ | 6.95 | 10.32 | 13.24 | 16.74 | 20.60 |
| $2.122 \times 10^8$ | 7.10 | 11.22 | 13.63 | 17.12 | 20.92 |
| $2.177 \times 10^8$ | 7.05 | 11.42 | 13.64 | 17.06 | 20.99 |
| $2.324 \times 10^8$ | 7.08 | 11.52 | 13.68 | 17.07 | 20.99 |
| $2.583 \times 10^8$ | 7.13 | 11.77 | 13.78 | 17.27 | 21.02 |

TABLE 2-continued

Insertion Phase Difference Phase (in degrees)

| Frequency (Hz) | Brain Damage | Brain Hemorrhage | Stroke | Healthy Brain | Tumor |
|---|---|---|---|---|---|
| $2.67 \times 10^8$ | 7.30 | 11.85 | 13.96 | 17.43 | 21.20 |
| $2.8 \times 10^8$ | 7.50 | 11.99 | 13.99 | 17.31 | 21.27 |
| $3.063 \times 10^8$ | 7.56 | 12.23 | 14.23 | 17.78 | 21.71 |
| $3.33 \times 10^8$ | 8.13 | 12.15 | 14.07 | 17.65 | 21.43 |

TABLE 3

Insertion Phase Difference Phase (in degrees)

| Frequency (Hz) | Healthy Brain | Tumor |
|---|---|---|
| $8.2 \times 10^7$ | 12.13 | 19.33 |
| $9.333 \times 10^7$ | 13.23 | 19.56 |
| $11.456 \times 10^7$ | 13.24 | 18.73 |
| $2.122 \times 10^8$ | 13.63 | 20.04 |
| $2.177 \times 10^8$ | 13.64 | 20.16 |
| $2.324 \times 10^8$ | 13.68 | 20.08 |
| $2.583 \times 10^8$ | 13.78 | 20.23 |
| $2.67 \times 10^8$ | 13.96 | 20.33 |
| $2.8 \times 10^8$ | 13.99 | 19.59 |
| $3.063 \times 10^8$ | 14.23 | 19.93 |
| $3.33 \times 10^8$ | 14.07 | 19.66 |

Figure 12:
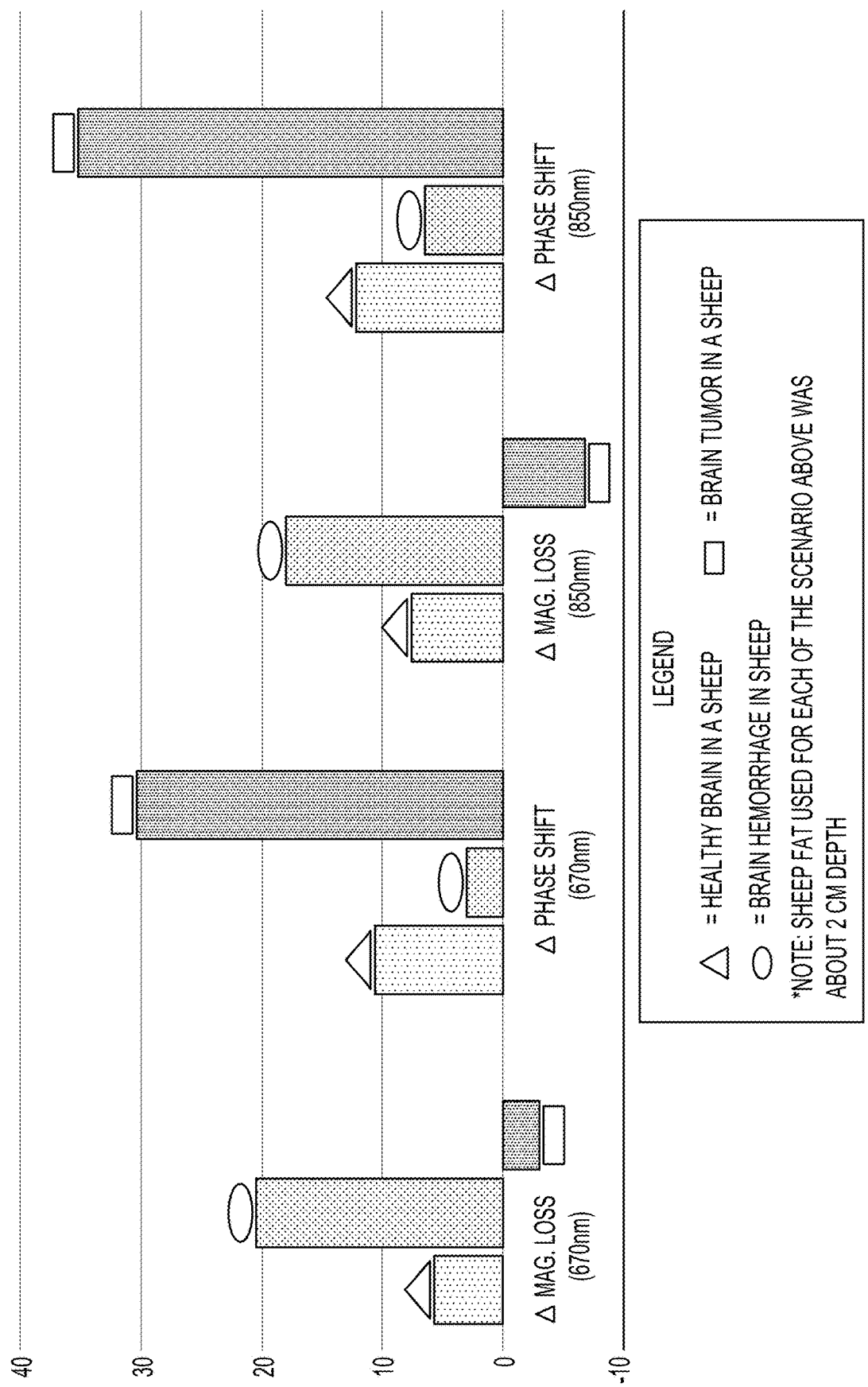
FIG. 12 is a graph comparing A magnitude loss and A phase shift results for the method of detecting brain abnormalities using backscattered light for cases including a sheep having a healthy brain, a brain tumor, and a brain hemorrhage using sheep fat at about 2 cm depth.
Figure 13:
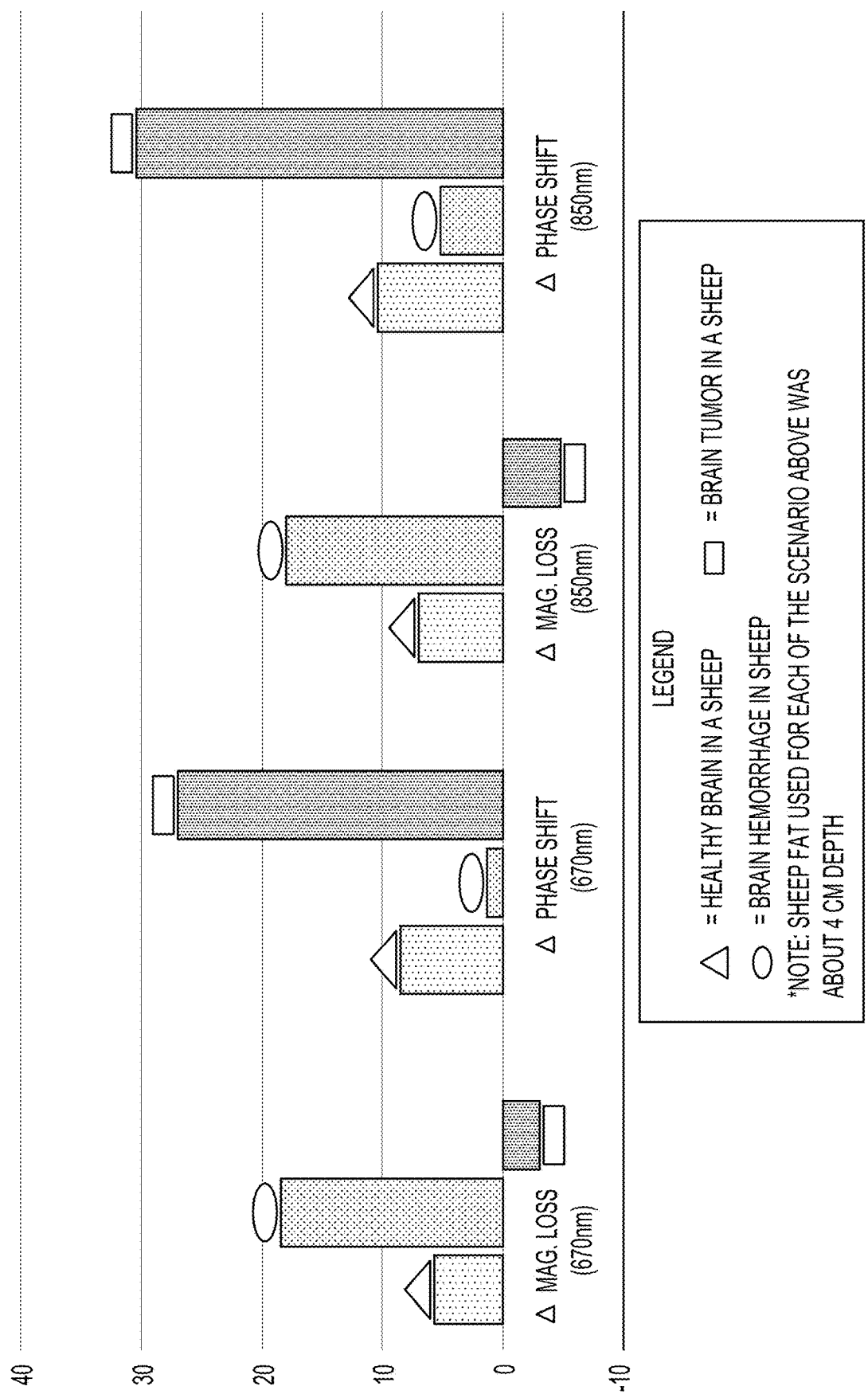
FIG. 13 is a graph comparing A magnitude loss and A phase shift results for the method of detecting brain abnormalities using backscattered light for cases including a sheep having a healthy brain, a brain tumor, and a brain hemorrhage using sheep fat at about 4 cm depth.

FIGS. 12-13 show healthy sheep fat with India ink to simulate a healthy brain, sheep fat with a higher level of India ink to simulate a brain hemorrhage, and sheep fat with jelly candies therein to simulate brain tumors with the respective size depths (about 2 cm depth in FIG. 12 and about 4 cm depth in FIG. 13) of the sheep fat. As shown in FIGS. 12-13, the brain hemorrhage and brain tumors have the highest Δ magnitude loss (insertion loss ($I_L$)) and the lowest Δ magnitude loss, respectively, for wavelengths of 670 nm and 850 nm at about 2 cm depth (FIG. 12) and about 4 cm depth (FIG. 13) of sheep fat. However, the brain tumors and brain hemorrhage have the highest Δ phase shift (insertion phase difference ($I_{PD}$)) and the lowest Δ phase shift, respectively, for wavelengths of 670 nm and 850 nm at about 2 cm depth (FIG. 12) and about 4 cm depth (FIG. 13) of sheep fat. Corresponding data are shown in Tables 4-5, respectively showing the data for about 2 cm depth (FIG. 12) and about 4 cm depth (FIG. 13) of sheep fat with Δ magnitude loss and Δ phase shift at 670 nm and 850 nm.

TABLE 4

| | Δ Magnitude Loss (670 nm) | Δ Phase Shift (670 nm) | Δ Magnitude Loss (850 nm) | Δ Phase Shift (850 nm) |
|---|---|---|---|---|
| Healthy fat w/about 2 cm depth | 5.89 | 10.56 | 7.68 | 12.33 |
| Hemorrhage w/about 2 cm depth | 20.6 | 3.22 | 18.11 | 6.55 |
| Tumor w/ about 2 cm depth | -3.25 | 30.33 | -6.72 | 35.56 |

TABLE 5

|  | Δ Magnitude Loss (670 nm) | Δ Phase Shift (670 nm) | Δ Magnitude Loss (850 nm) | Δ Phase Shift (850 nm) |
|---|---|---|---|---|
| Healthy fat w/about 4 cm depth | 5.89 | 8.57 | 7.23 | 10.53 |
| Hemorrhage w/about 4 cm depth | 18.40 | 1.40 | 17.99 | 5.23 |
| Tumor w/ about 4 cm depth | −3.25 | 27.33 | −5.02 | 30.80 |

Figure 14:
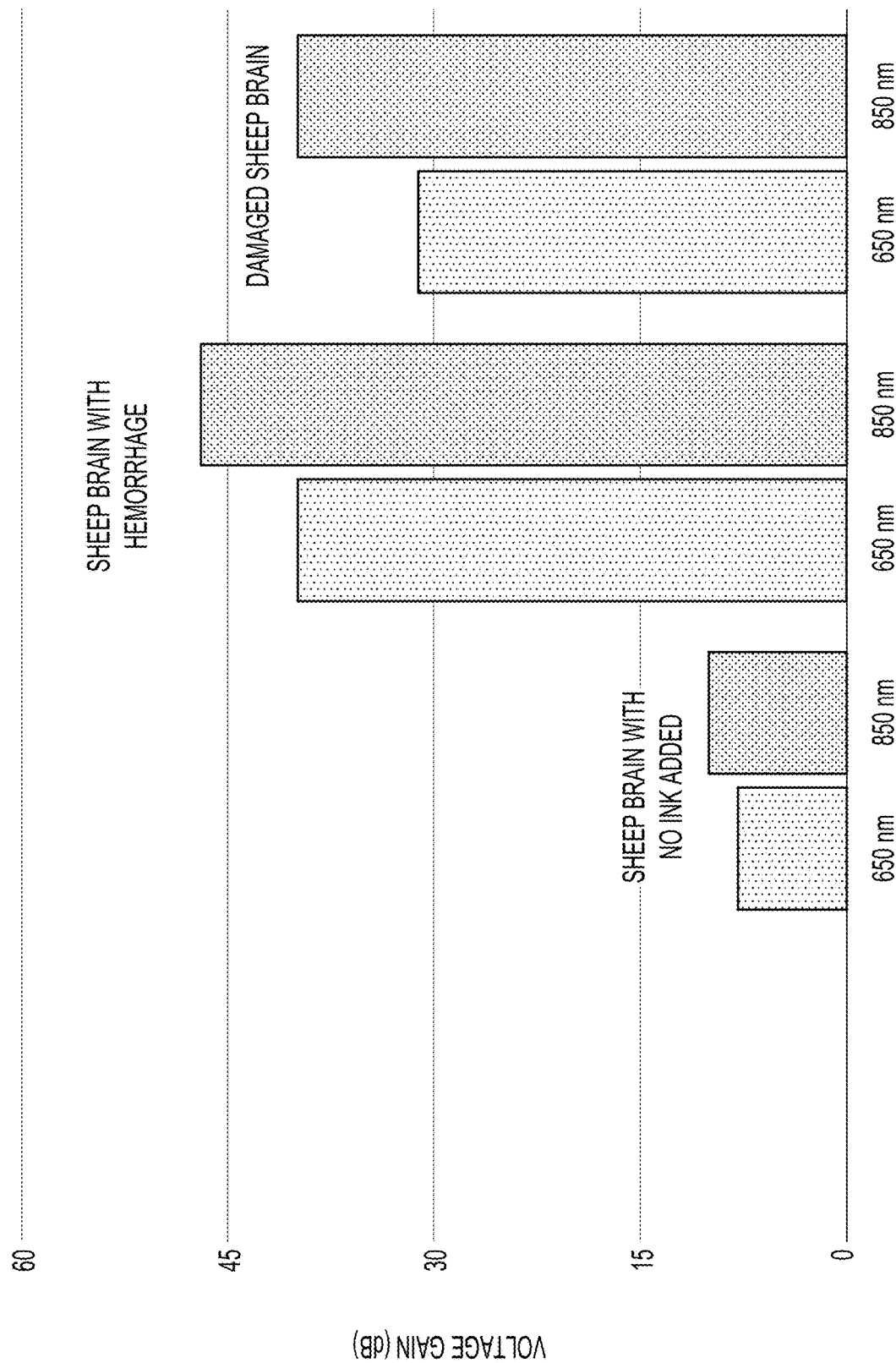
FIG. 14 is a graph comparing voltage gain results for the method of detecting brain abnormalities using backscattered light for cases including a sheep having a healthy brain, a brain damage, and a brain hemorrhage.

FIG. 14 depicts a sheep brain with no ink added to simulate a healthy brain, a sheep brain infused with India ink to simulate a brain hemorrhage, and a sheep brain with India ink and jelly candy to simulate a brain damaged with corresponding wavelengths. As shown in the figure, the sheep brain with the hemorrhage has the most voltage gains of about 40 dB and about 47 dB at about 650 nm and about 850 nm, respectively. On the other hand, sheep brain with no ink added has the lowest voltage gains of about 8 dB and about 10 dB at about 650 nm and about 850 nm, respectively. Corresponding data is shown in Table 6, showing the voltage gain at 650 nm and 850 nm for various sheep brain conditions.

TABLE 6

| Sheep Brain Conditions | 650 nm (voltage gain in dB) | 850 nm (voltage gain in dB) |
|---|---|---|
| Sheep brain w/ no ink added | 8 | 10 |
| Sheep brain w/ hemorrhage | 40 | 47 |
| Damaged sheep brain | 31 | 40 |

Figure 15:
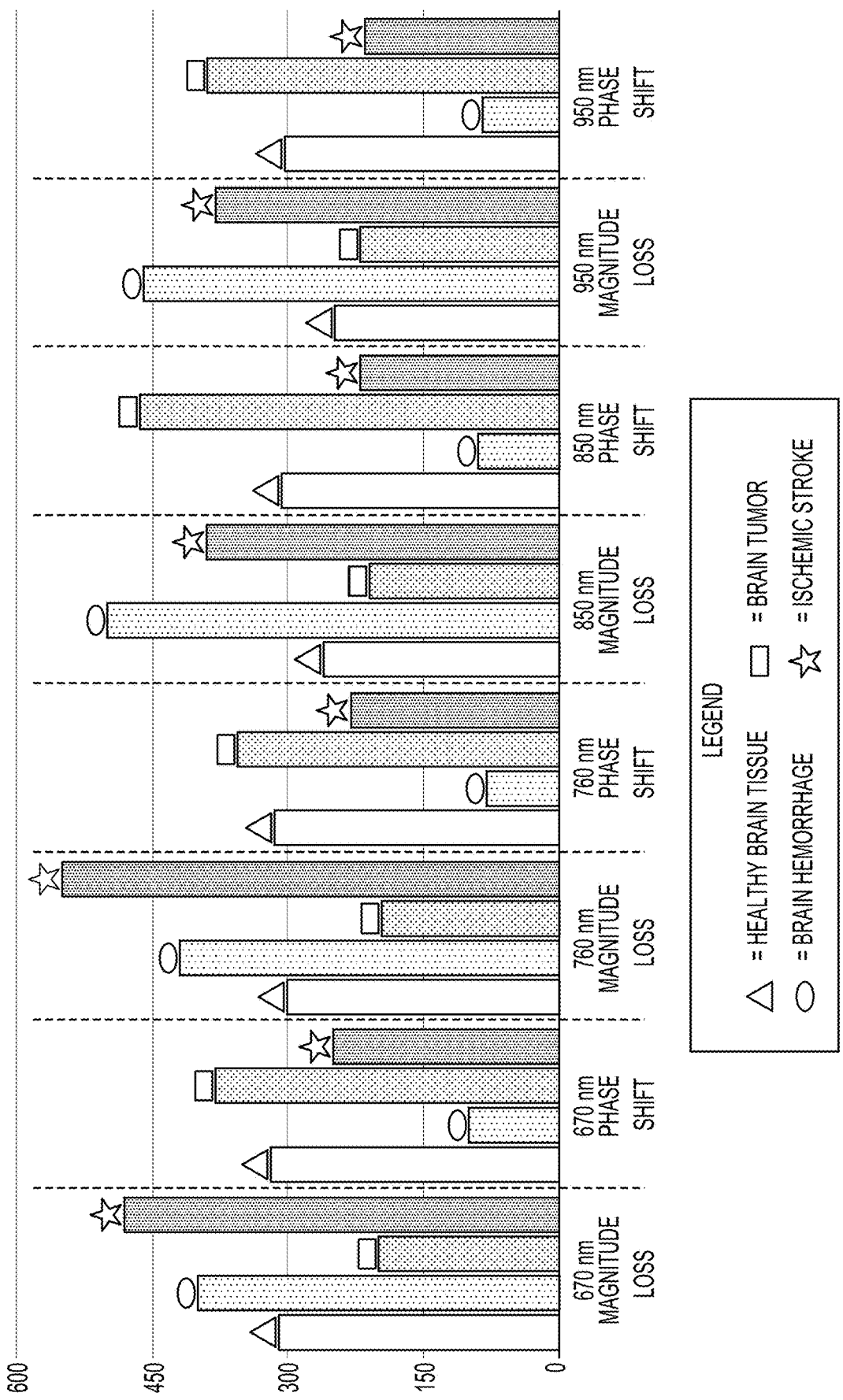
FIG. 15 is a graph comparing A magnitude loss and A phase shift results for the method of detecting brain abnormalities using backscattered light for cases including a sheep having a healthy brain, and a brain hemorrhage, a brain tumor, and a brain ischemic stroke.

FIG. 15 depicts absorption (magnitude loss) and scattering (phase shift) of NIR light at various wavelengths for various sheep brain conditions (i.e., sheep healthy brain tissue, a sheep brain with India ink to simulate a brain hemorrhage, a sheep brain with jelly candy to simulate brain tumors, and a sheep brain with an external device placed therein to gently exert pressure on the cerebral artery thereby imitating blockage to simulate ischemic stroke). As shown in the figure, ischemic stroke has the highest magnitude loss at 670 nm and 760 nm due to the deoxygenated hemoglobin being sensitive to those wavelengths. However, at 850 nm and 950 nm, the brain hemorrhage has the highest magnitude loss due to oxygenated hemoglobin being sensitive to those wavelengths. For all the wavelengths, the tumors have the lowest magnitude loss. As for phase shift, the brain tumors have the highest phase shift for all the wavelengths which indicate high scattering of NIR light due to heterogeneous nature of tumor tissue. Conversely, the brain hemorrhage has the lowest phase shift for all the wavelengths, which indicates low scattering of NIR light due to homogeneous nature of pooling blood. Corresponding data is shown in Table 7, showing the magnitude loss and phase shift at various wavelengths for various sheep brain conditions.

TABLE 7

| Sheep Brain Conditions | Mag. Loss (670 nm) | Phase Shift (670 nm) | Mag. Loss (760 nm) | Phase Shift (760 nm) | Mag. Loss (850 nm) | Phase Shift (850 nm) | Mag. Loss (950 nm) | Phase Shift (950 nm) |
|---|---|---|---|---|---|---|---|---|
| Healthy brain tissue | 310 | 320 | 300 | 315 | 260 | 310 | 250 | 305 |
| Brain hemorrhage | 400 | 100 | 420 | 80 | 500 | 90 | 460 | 85 |
| Brain tumor | 200 | 380 | 200 | 360 | 210 | 465 | 220 | 390 |
| Ischemic stroke | 480 | 250 | 550 | 230 | 390 | 220 | 380 | 215 |

It is to be understood that the system and method for detecting brain abnormalities using backscattered radiation are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

What is claimed is:

1. A method of detecting brain abnormalities in a brain of a patient using backscattered light, the method comprising the steps of:
    generating at least one pulsed incident beam of light with at least one light source;
    directing the at least one pulsed incident beam of light toward a portion of the brain of the patient;
    receiving at least one backscattered beam of light from the portion of the patient's brain;
    calculating an insertion loss, $I_L$, as $$I_L = 20\log\frac{A_{BS}}{A_I},$$

wherein $A_{BS}$ is an amplitude of the at least one backscattered beam of light, and wherein $A_I$ is an amplitude of the at least one pulsed incident beam of light;
    calculating an insertion phase difference, $I_{PD}$, as $I_{PD}=\phi_{BS}-\phi_I$, wherein $\phi_{BS}$ is a phase of the at least one backscattered beam of light, and wherein $\phi_I$ is a phase of the at least one pulsed incident beam of light; and
    determining if the patient has a brain abnormality based on the calculated insertion loss and the insertion phase difference,
    wherein the brain of the patient is determined to have a hemorrhage when the calculated insertion loss is above a first loss threshold and the calculated insertion phase difference is lower than a first phase threshold,
    wherein the brain of the patient is determined to have healthy brain tissue when the calculated insertion loss is lower than a second loss threshold and the calculated insertion phase difference is higher than a second phase threshold,
    wherein the brain of the patient is determined to have at least one tumor if the calculated insertion loss is between the first and second loss thresholds and the calculated insertion phase difference is higher than the first and second phase thresholds, and
    wherein the brain of the patient is determined to have an ischemic stroke if the calculated insertion loss is between the first and second loss thresholds and the calculated insertion phase difference is higher than the first and second phase thresholds but lower than that determined for the brain tumor.

2. The method of detecting the brain abnormalities in the brain of the patient using backscattered light of claim 1, wherein the at least one pulsed incident beam of light is generated by a vertical-cavity surface-emitting laser.

3. The method of detecting the brain abnormalities in the brain of the patient using backscattered light of claim 1, wherein the at least one pulsed incident beam of light comprises near infrared light.

4. The method of detecting the brain abnormalities in the brain of the patient using backscattered light of claim 1, wherein the at least one pulsed incident beam of light is generated by four light sources, wherein the at least one pulsed incident beam of light comprises four pulsed incident beams of light, and wherein each of the four pulsed incident beams of light has a unique wavelength associated therewith.

5. The method of detecting the brain abnormalities in the brain of the patient using backscattered light of claim 4, wherein the four pulsed incident beams of light have respective wavelengths of about 650 nm to about 680 nm, about 760 nm, about 850 nm, and about 980 nm.

6. The method of detecting the brain abnormalities in the brain of the patient using backscattered light of claim 1, further comprising measuring the backscattered amplitude and the backscattered phase using a comparator microchip prior to the steps of calculating the insertion loss and calculating the insertion phase difference.

7. The method of detecting the brain abnormalities in the brain of the patient using backscattered light of claim 1, further comprising:
training a machine learning system with at least one of the first loss threshold, the second loss threshold, the first phrase threshold, and the second phrase threshold to obtain training data; and
comparing the calculated insertion loss and the insertion phase difference with the training data.

8. The method of detecting the brain abnormalities in the brain of the patient using backscattered light of claim 1, wherein the at least one pulsed incident beam of light is pulsed with a frequency of about 30 MHz to about 1000 MHz.

9. A system for detecting brain abnormalities in a brain of a patient using backscattered light, the system comprising:
a headband configured to be worn on a head of a patient, wherein the headband comprises:
at least one light source configured to generate at least one pulsed incident beam of light directed toward a portion of the brain of the patient;
at least one detector configured to detect at least one backscattered beam of light from the portion of the brain of the patient; and
a controller configured to calculate an insertion loss, $I_L$, as $$I_L = 20\log\frac{A_{BS}}{A_I}$$

and an insertion phase difference, $I_{PD}$, as $I_{PD}=\phi_{BS}-\phi_I$, wherein $A_{BS}$ is an amplitude of the at least one backscattered beam of light, wherein A is an amplitude of the at least one pulsed incident beam of light, wherein $\phi_{BS}$ is a phase of the at least one backscattered beam of light, and wherein $\phi_I$ is a phase of the at least one pulsed incident beam of light; and
a computer configured to connect to the headband,
wherein the controller is configured to determine if the patient has a brain abnormality based on the calculated insertion loss and the insertion phase difference,
wherein the brain of the patient is determined to have a hemorrhage when the calculated insertion loss is above a first loss threshold and the calculated insertion phase difference is lower than a first phase threshold,
wherein the brain of the patient is determined to have healthy brain tissue when the calculated insertion loss is lower than a second loss threshold and the calculated insertion phase difference is higher than a second phase threshold,
wherein the brain of the patient is determined to have at least one tumor if the calculated insertion loss is between the first and second loss thresholds and the calculated insertion phase difference is higher than the first and second phase thresholds, and
wherein the brain of the patient is determined to have an ischemic stroke if the calculated insertion loss is between the first and second loss thresholds and the calculated insertion phase difference is higher than the first and second phase thresholds but lower than that determined for the brain tumor.

10. The system for detecting the brain abnormalities in the brain of the patient using backscattered light of claim 9, wherein the at least one light source comprises a vertical-cavity surface-emitting laser.

11. The system for detecting the brain abnormalities in the brain of the patient using backscattered light of claim 9, wherein the at least one light source comprises four light sources, the at least one pulsed incident beam of light comprises four pulsed incident beams of light, and wherein each of the four pulsed incident beams of light has a unique wavelength.

12. The system for detecting the brain abnormalities in the brain of the patient using backscattered light of claim 11, wherein the headband further comprises a plurality of elements mounted on an exterior surface of a housing of the headband, wherein each of the plurality of elements comprises a plurality of light projections configured to direct the pulsed incident beam of light from each of the four light sources toward the portion of the patient's brain, and wherein the at least one detector comprises a plurality of detectors, the plurality of detectors being respectively mounted on the plurality of elements.

13. The system for detecting the brain abnormalities in the brain of the patient using backscattered light of claim 9, wherein the computer comprises a machine learning system configured to be trained with at least one of the first loss threshold, the second loss threshold, the first phrase threshold, and the second phrase threshold to obtain training data, and wherein the computer is configured to compare the insertion loss and the insertion phase difference with the training data.

14. The system for detecting the brain abnormalities in the brain of the patient using backscattered light of claim 9, wherein the headband further comprises at least one LED light indicator mounted on an exterior surface of a housing of the headband configured to display a predetermined color based on the detected brain abnormality determined by the controller.

15. The system for detecting the brain abnormalities in the brain of the patient using backscattered light of claim 9, wherein the at least one pulsed incident beam of light is pulsed with a frequency of about 30 MHz to about 1000 MHz from a radio frequency generator via a radio frequency switch.

16. The system for detecting the brain abnormalities in the brain of the patient using backscattered light of claim 9, wherein the headband further comprises a calibration button and a reset button configured for scanning of a healthy portion of the patient's brain and diagnostic scanning for detecting the brain abnormalities, respectively.

\* \* \* \* \*